(12) United States Patent
Nakamura

(10) Patent No.: US 12,290,394 B2
(45) Date of Patent: May 6, 2025

(54) CONDITION DETERMINATION DEVICE, NON-TRANSITORY RECORDING MEDIUM, AND CONDITION DETERMINATION METHOD

(71) Applicant: Konica Minolta, Inc., Tokyo (JP)

(72) Inventor: Ikki Nakamura, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 162 days.

(21) Appl. No.: 18/146,224

(22) Filed: Dec. 23, 2022

(65) Prior Publication Data

US 2023/0218259 A1 Jul. 13, 2023

(30) Foreign Application Priority Data

Jan. 12, 2022 (JP) .................. 2022-002781

(51) Int. Cl.
*A61B 6/00* (2024.01)
(52) U.S. Cl.
CPC ............ *A61B 6/541* (2013.01); *A61B 6/4494* (2013.01)
(58) Field of Classification Search
CPC ....... A61B 6/541; A61B 6/4494; A61B 6/488; A61B 6/5229; A61B 6/545
See application file for complete search history.

(56) References Cited

U.S. PATENT DOCUMENTS

2005/0111614 A1* 5/2005 Matsuura ............... A61B 6/488
378/19

FOREIGN PATENT DOCUMENTS

JP 2020110444 A 7/2020
JP 2020-199163 A 12/2020

OTHER PUBLICATIONS

Notice of Reasons for Refusal, dated Mar. 5, 2025, issued for the corresponding Japanese Patent Application No. 2022-002781, 6 pages.

* cited by examiner

*Primary Examiner* — Courtney D Thomas
(74) *Attorney, Agent, or Firm* — LUCAS & MERCANTI, LLP

(57) ABSTRACT

A condition determination device includes a hardware processor that: acquires sensor information obtained by detecting information regarding a subject to be radiographed by using a sensor and order information regarding a radiographing order; and determines a radiographing condition by inputting the sensor information and the order information to a trained identifier.

17 Claims, 4 Drawing Sheets

CONDITION DETERMINATION DEVICE, NON-TRANSITORY RECORDING MEDIUM, AND CONDITION DETERMINATION METHOD

CROSS-REFERENCE TO RELATED APPLICATION

Japanese patent application No. 2022-2781 filed on Jan. 12, 2022, including description, claims, drawings, and abstract the entire disclosure is incorporated herein by reference in its entirety.

BACKGROUND

Technological Field

The present invention relates to a condition determination device, a non-transitory recording medium, and a condition determination method.

Description of the Related Art

When performing radiograph on a predetermined site of a subject, a radiographer sets a condition for each device based on a radiographing order from a medical doctor, and performs radiographing. In addition to the condition setting for each device, a body posture or the like of the subject at the time of radiographing, that is, a state of the subject at the time of radiographing also affects a radiographic image (refer to Unexamined Japanese Patent Publication No. 2020-199163).

SUMMARY

When the radiographic image is captured, it is desirable to prevent the state of the subject from affecting the radiological image.

The present invention is achieved in view of the problems described above, and an object of the present invention is to provide a condition determination device capable of preventing a state of a subject from affecting a radiographic image, a non-transitory recording medium, and a condition determination method.

To achieve at least one of the above-mentioned objects, according to an aspect of the present invention, a condition determination device reflecting one aspect of the present invention comprising a hardware processor that: acquires sensor information obtained by detecting information regarding a subject to be radiographed by using a sensor and order information regarding a radiographing order; and determines a radiographing condition by inputting said sensor information and said order information to a trained identifier.

The objects, features, and characteristics of this invention other than those set forth above will become apparent from the description given herein below with reference to preferred embodiments illustrated in the accompanying drawings.

BRIEF DESCRIPTION OF THE DRAWING

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
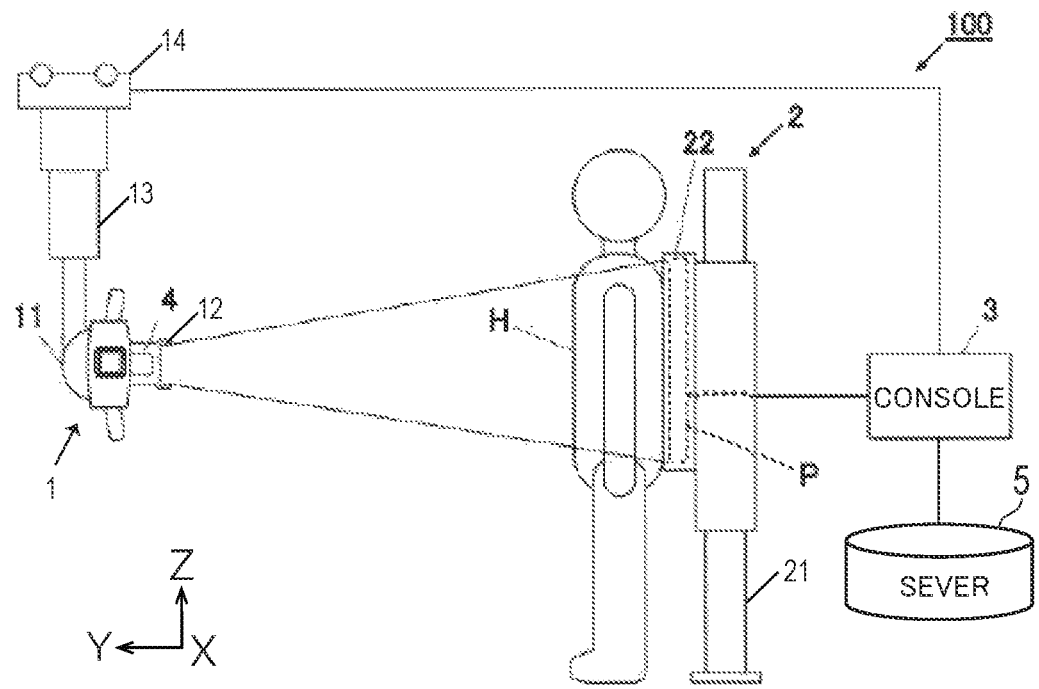
FIG. 1 is a diagram illustrating an overall configuration of a radiographic image capturing system.

Hereinafter, one or more embodiments of the present invention will be described with reference to the drawings. However, the scope of the invention is not limited to the disclosed embodiments.

Hereinafter, the embodiments of the present invention will be described with reference to the accompanying drawings. Note that in the description of the drawings, the same elements are denoted by the same reference numerals, and the overlapping description will be omitted. Furthermore, dimensional ratios in the drawings are exaggerated for convenience of description, and may be different from actual ratios.

<Overall Configuration of Radiographic Image Capturing System 100>

FIG. 1 is a diagram illustrating an overall configuration of a radiographic image capturing system 100 according to the present embodiment.

The radiographic image capturing system 100 irradiates a predetermined site of a subject H with radiation to generate a radiographic image. The radiographic image capturing system 100 includes, for example, a radiation irradiation device 1, a radiation detection device 2, a console 3, an optical camera 4, and a server 5. For example, the radiation irradiation device 1, the radiation detection device 2, the optical camera 4 and the server 5 are each connected to the console 3 via a network. Here, the console 3 corresponds to a specific example of a condition determination device of the present invention, and the optical camera 4 corresponds to a specific example of a sensor of the present invention.

The radiation irradiation device 1 irradiates the predetermined site of the subject H with radiation (X-ray) in accordance with the control of the console 3. The console 3 outputs, to the radiation irradiation device 1, pieces of information regarding, for example, a dose, a tube current, a tube voltage, a radiation irradiation time, an mAs value (tube current time product), a source to image receptor distance (SID), a radiation irradiation direction, a radiation irradiation range, and the like as an irradiation condition. The radiation irradiation device 1 includes, for example, a radiation source 11, a collimator 12, a holder 13, and a movement mechanism 14.

The radiation source 11 is provided at a position opposed to the radiation detection device 2 with the subject H therebetween. The radiation source 11 includes, for example, an X-ray tube, and generates a predetermined dose of the radiation (X-ray) for a predetermined time. In the following description, a direction in which the radiation source 11 is opposed to the radiation detection device 2 is referred to as a Y direction, a gravity direction is referred to as a Z direction, and a direction perpendicular to the Y direction and the Z direction is referred to as an X direction.

The collimator 12 is disposed between the radiation source 11 and the subject H. An irradiation direction and irradiation range of the radiation generated by the radiation source 11 is defined by the collimator 12. The collimator 12 has, for example, an opening, and shielding and exposure of the opening are controlled by the console 3.

The holder 13 holds the radiation source 11 and the collimator 12. The holder 13 holds, for example, the radiation source 11 and the collimator 12 such that the radiation source 11 and the collimator 12 are movable up and down, that is, movable in the Z direction.

The movement mechanism 14 includes, for example, a drive unit such as a motor. The movement mechanism 14 moves the radiation source 11 and the collimator 12 in the X direction and the Y direction and moves the holder 13 in the Z direction, for example, in accordance with the control of the console 3. The movement mechanism 14 moves the radiation source 11 and the collimator 12 in the X direction and the Y direction by using, for example, a rail.

The radiation detection device 2 includes, for example, a support column 21, a detector holder 22, and a radiation detector P. The support column 21 has a predetermined width in the X direction and extends in the Z direction. The radiation detector P held by the detector holder 22 is attached to the support column 21.

For example, the detector holder 22 holds the radiation detector P therein. The detector holder 22 is configured to be movable, for example, in the X direction and the Z direction. For example, the subject H stands in contact with the detector holder 22, and radiographing is performed.

The radiation detector P includes a flat panel detector (FPD) or the like. The radiation detector P detects the radiation emitted from the radiation source 11 and transmitted through the subject H. The radiation detector P includes, for example, a substrate on which a plurality of detection elements (pixels) are disposed in a matrix. Each of the detection elements detects radiation, converts the detected radiation into an electrical signal, and accumulates the electrical signal. Each of the pixels is provided with a switching element such as a thin film transistor (TFT). The switching element is controlled, for example, based on a reading condition input from the console 3, and the electrical signal accumulated in each pixel is sent to the console 3.

The console 3 is, for example, a computer such as a personal computer (PC), a smartphone, or a tablet terminal. The console 3 outputs a radiation irradiation condition to the radiation irradiation device 1 and outputs the reading condition to the radiation detection device 2. Accordingly, the radiographing by the radiation irradiation device 1 and an operation of reading the radiographic image by the radiation detection device 2 are controlled.

Figure 2:
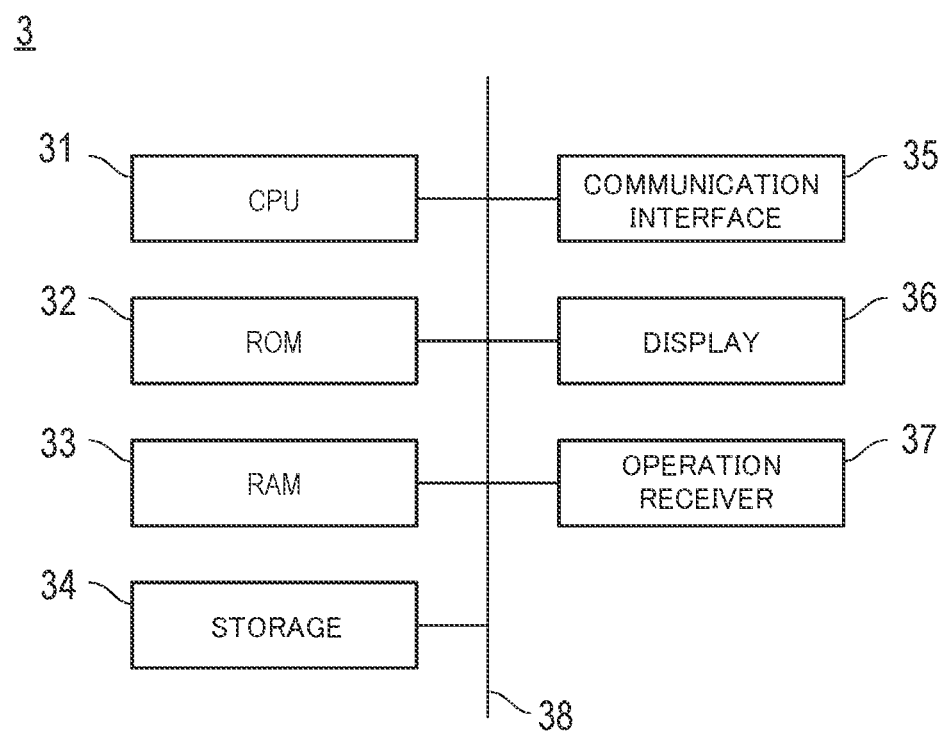
FIG. 2 is a block diagram illustrating a schematic configuration of a console illustrated in FIG. 1.

FIG. 2 is a block diagram illustrating an example of a schematic configuration of the console 3. The console 3 includes, for example, a central processing unit (CPU) 31, a read only memory (ROM) 32, a random access memory (RAM) 33, a storage 34, a communication interface 35, a display 36, and an operation receiver 37. Each of the configurations is communicably connected to each other via a bus 38.

The CPU 31 performs control of each of the above-described configurations and various types of arithmetic processing according to programs stored in the ROM 32 and the storage 34. A specific function of the CPU 31 will be described later.

The ROM 32 stores various programs and various data.

The RAM 33 temporarily stores programs and data as a work area.

The storage 34 stores various programs including an operating system and various data. For example, in the storage 34, an application for determining a radiographing condition from sensor information and order information to be described later by using a trained identifier is installed. Furthermore, in the storage 34, information regarding the radiographic image acquired from the radiation detection device 2 may be stored. In the storage 34, patient information (medical record information) of the subject H may be stored. Furthermore, in the storage 34, a trained model used as an identifier and training data used for machine learning may be stored.

The communication interface 35 is an interface for communicating with other devices. As the communication interface 35, a communication interface according to various wired or wireless standards is used. For example, the communication interface 35 is used for receiving information regarding a radiographic image from the radiation detection device 2 or the server 5 or transmitting a radiation irradiation condition to the radiation irradiation device 1.

The display 36 includes a liquid crystal display (LCD), an organic EL display, and the like, and displays various information. The display 36 may be configured by viewer software, a printer, or the like.

Figure 3:
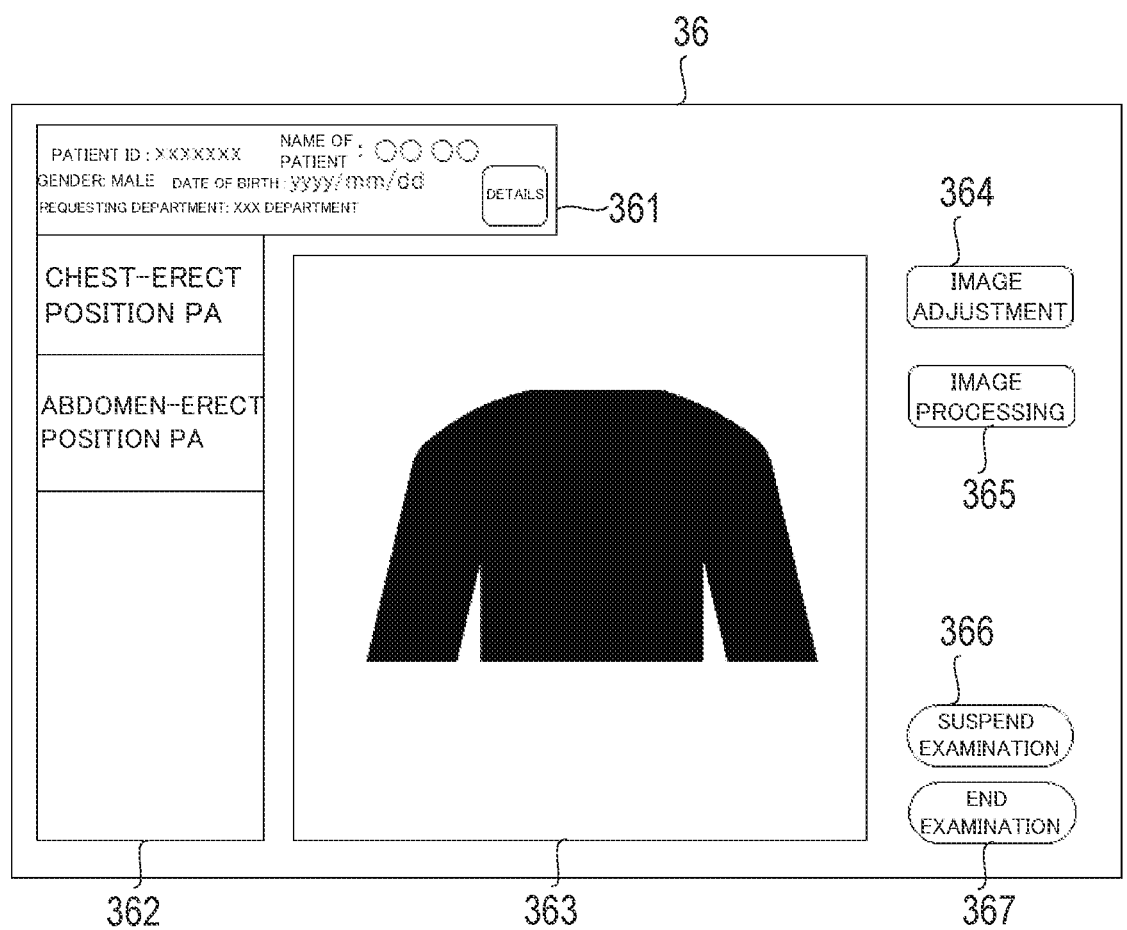
FIG. 3 is a view illustrating an example of a display state of a display illustrated in FIG. 2.

FIG. 3 illustrates an example of a screen displayed on the display 36. For example, a screen including a patient information display area 361, an examination information display area 362, an image display area 363, an image adjustment button 364, an image processing button 365, an examination suspension button 366, and an examination end button 367 is displayed on the display 36.

In the patient information display area 361, patient information of the subject H to be radiographed is displayed. In the patient information display area 361, for example, information regarding a patient ID, a name, a gender, a date of birth, a department requesting radiographing, and the like for the subject H is displayed.

In the examination information display area 362, information regarding a site to be radiographed, a radiographing direction, and the like instructed by the department requesting radiographing is displayed. In the image display area 363, a radiographic image obtained by photographing a predetermined site of the subject H is displayed. For example, the console 3 outputs the captured radiographic image to the server 5.

The image adjustment button 364 and the image processing button 365 are buttons operated when the adjusting and processing for the captured radiographic image are performed. Specifically, by operating the image adjustment button 364 and the image processing button 365, enlargement and reduction, rotation and inversion, region of interest (ROI) setting, masking, removal of scattered radiation, a contrast adjustment, a luminance adjustment, text input, and the like can be performed for radiographic image data. The examination suspension button 366 is a button operated when the examination is suspended, and the examination end button 367 is a button operated when the examination is ended.

The operation receiver 37 includes a touch sensor, a pointing device such as a mouse, a keyboard, and the like, and receives various operations of a user. Note that the display 36 and the operation receiver 37 may constitute a touch panel by superimposing a touch sensor as the operation receiver 37 on a display surface as the display 36.

The optical camera 4 acquires an optical image of the subject H to be radiographed. The optical image of the subject H acquired by the optical camera 4 is output to the console 3. The optical camera 4 acquires an optical image including the subject H and surroundings of the subject H, an optical image including the entire body of the subject H, an optical image of a site to be radiographed, or the like. The optical camera 4 is provided, for example, in the vicinity of the collimator 12. The optical camera 4 may be configured to be movable in the X direction, the Y direction, and the Z direction. The optical camera 4 includes, for example, a visible light camera, an infrared camera, or the like. The radiographic image capturing system 100 may include a plurality of the optical cameras 4. In the present embodiment, since the radiographic image capturing system 100 includes the optical camera 4, it is possible to detect the state of the subject H at the time of radiographing. As will be described in detail later, accordingly, the radiographing condition corresponding to the radiographing order can be determined according to the state of the subject H. Although details will be described later, this makes it possible to prevent the state of the subject from affecting the radiographic image.

The server 5 acquires and stores, for example, a result obtained by processing of the console 3. Patient information, examination information, and the like for the subject H may be stored in the server 5. For example, the console 3 acquires, from the server 5, information regarding a radiographing order for the subject H (order information to be described later). The server 5 may acquire information regarding a radiographic image and information regarding an optical image, and the console 3 may acquire information regarding a radiographic image and information regarding an optical image from the server 5. The console 3 may be connected to a hospital information system (HIS), a radiology information system (RIS), a picture archiving and communication system (PACS), an electronic medical record, or the like.

<Function of Console 3>

Figure 4:
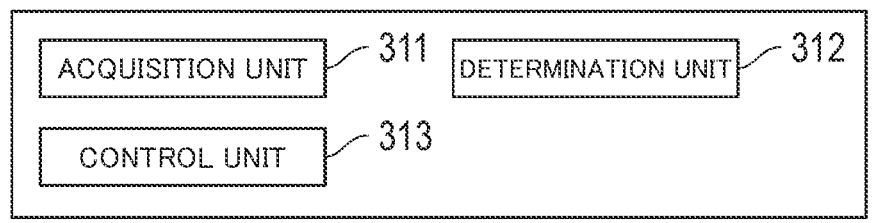
FIG. 4 is a block diagram illustrating a functional configuration of the console illustrated in FIG. 1.

FIG. 4 is a block diagram illustrating a functional configuration of the console 3. The console 3 functions as an acquisition unit 311, a determination unit 312, and a control unit 313 when the CPU 31 reads a program stored in the storage 34 and executes processing. The console 3 determines a radiographing condition according to the radiographing order corresponding to the state of the subject H immediately before the radiographing, and controls the radiation irradiation device 1 and the radiation detection device 2 based on the determined radiographing condition.

The acquisition unit 311 acquires sensor information and order information. The sensor information is, for example, information regarding the state of the subject H detected using the optical camera 4, and specifically, is image information of the subject H captured by the optical camera 4. The sensor information includes, for example, at least one of information regarding a position (positioning) of the subject H before a start of radiation irradiation, information regarding the body posture of the subject H before the start of radiation irradiation, or information regarding the site to be radiographed of the subject H. The sensor information may be information other than the image information, and may be, for example, information regarding a distance between the subject H and the radiation source 11, information regarding a body mass index (BMI) of the subject H, information regarding a body thickness of the subject H, or the like.

The order information is information regarding the radiographing order for the subject H, and includes, for example, patient information and examination information of the subject H. In the patient information, for example, information regarding a patient ID, a name, a gender, a date of birth, a department requesting radiographing, and the like for the subject H is included. The examination information includes, for example, information regarding an examination ID, an examination date and time, a site to be radiographed, and a radiographing direction, or the like.

For example, the acquisition unit 311 acquires sensor information from the optical camera 4 and acquires order information from the server 5. The acquisition unit 311 may acquire the order information from the storage 34 or the like.

The determination unit 312 determines the radiographing condition by inputting the sensor information and order information acquired the acquisition unit 311 to the trained identifier. The determination unit 312 determines, for example, a radiation irradiation condition. The determination unit 312 determines, for example, the dose, the value of the tube current, the value of the tube voltage, the radiation irradiation time, the mAs value, the SID, the radiation irradiation direction, the radiation irradiation range, and the like as the irradiation conditions. Since the adjustment of the irradiation condition greatly affects the radiographic image, the determination unit 312 determines an appropriate irradiation condition. Therefore, an appropriate radiographic image can be easily obtained.

The determination unit 312 may determine a detection condition of the radiation detection device 2. The determination unit 312 determines, for example, a reading condition of the electrical signal accumulated in each pixel as the detection condition. The determination unit 312 may determine the irradiation condition and the detection condition.

The control unit 313 outputs the radiographing condition determined by the determination unit 312 to the radiation irradiation device 1 and the radiation detection device 2. Accordingly, the radiation irradiation by the radiation irradiation device 1 and the detection of radiation by the radiation detection device 2 are controlled.

<Processing Outline of Console 3>

The processing executed in the console 3 will be described in detail below.

Figure 5:
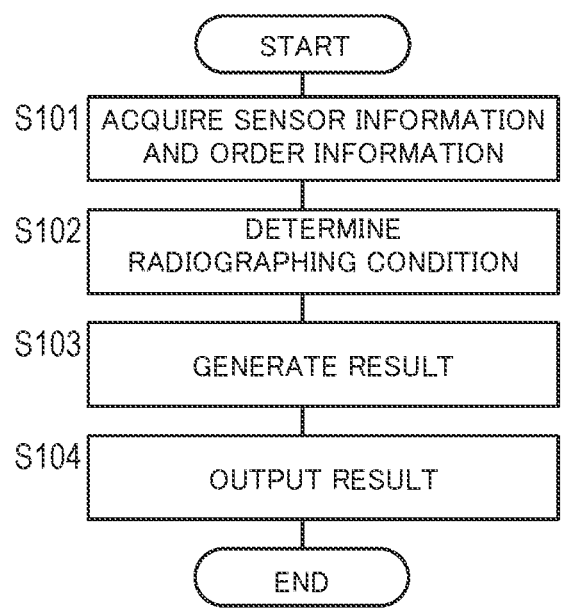
FIG. 5 is a flowchart illustrating a procedure of radiographing condition determination processing executed in the console illustrated in FIG. 1.

FIG. 5 is a flowchart illustrating a procedure of determination processing executed in the console 3. The processing of the console 3 illustrated in the flowchart of FIG. 5 is stored as a program in the storage 34 of the console 3, and is executed by the CPU 31 controlling each unit.

(Step S101)

First, the console 3 acquires sensor information and order information. For example, the console 3 acquires the sensor information by imaging the subject H by use of the optical camera 4 and acquires the order information from the server 5.

(Step S102)

The console 3 inputs the sensor information and order information acquired in the processing in Step S101 to the identifier trained in advance in a machine learning manner, and determines the radiographing condition of the subject H. For example, by a training method to be described later, the identifier is trained in a machine learning manner by using training data including sensor information and order information of a plurality of subjects in the past, which are prepared in advance, and information regarding a radiographing condition corresponding to sensor information and order information of each of the subjects. Specifically, the identifier is trained in a machine learning manner by using the sensor information and order information of a plurality of the subjects in the past as input data, and information regarding a radiographing condition corresponding to the sensor information and order information of each of the subjects as output data. Accordingly, the console 3 inputs the sensor information and order information acquired for the subject H to the identifier, and determines the radiographing condition of the subject H. For example, the console 3 determines at least one of an irradiation condition of the radiation irradiation device 1 or a detection condition of the radiation detection device 2 as a radiographing condition.
(Step S103)

The console 3 generates a determination result of the radiographing condition of the subject H based on the output by the identifier in the processing of Step S102.
(Step S104)

The console 3 outputs the determination result generated in the processing of Step S103 and ends the processing. For example, the console 3 outputs the radiation irradiation condition determined in the processing of Step S102 to the radiation irradiation device 1 and outputs the detection condition to the radiation detection device 2.

For example, the console 3 determines the irradiation range by controlling the collimator 12 when acquiring the order information regarding the site to be radiographed and position information of the subject H obtained by the optical camera. Accordingly, the radiation is emitted in an appropriate range, and it is possible to prevent a radiographing failure due to a deviation between the site to be radiographed and the irradiation range.

For example, the console 3 determines the irradiation direction of the radiation when acquiring the order information regarding the site to be radiographed and information regarding the body posture of the subject H obtained by the optical camera. Accordingly, for example, in a case where the body posture of the subject H is directed obliquely, an appropriate radiographic image can be easily obtained by irradiating the site to be radiographed with radiation from a front direction.

For example, when acquiring the information regarding the body thickness of the subject and the order information, the console 3 sets the irradiation condition corresponding to the body thickness of the subject from a standard irradiation condition set in advance and corresponding to the order. Accordingly, for example, by increasing the dose for the subject H having a thick body shape, an appropriate radiographic image can be easily obtained.

<Learning Processing>

Next, a machine learning method for a trained model used in the identifier will be described.

Figure 6:
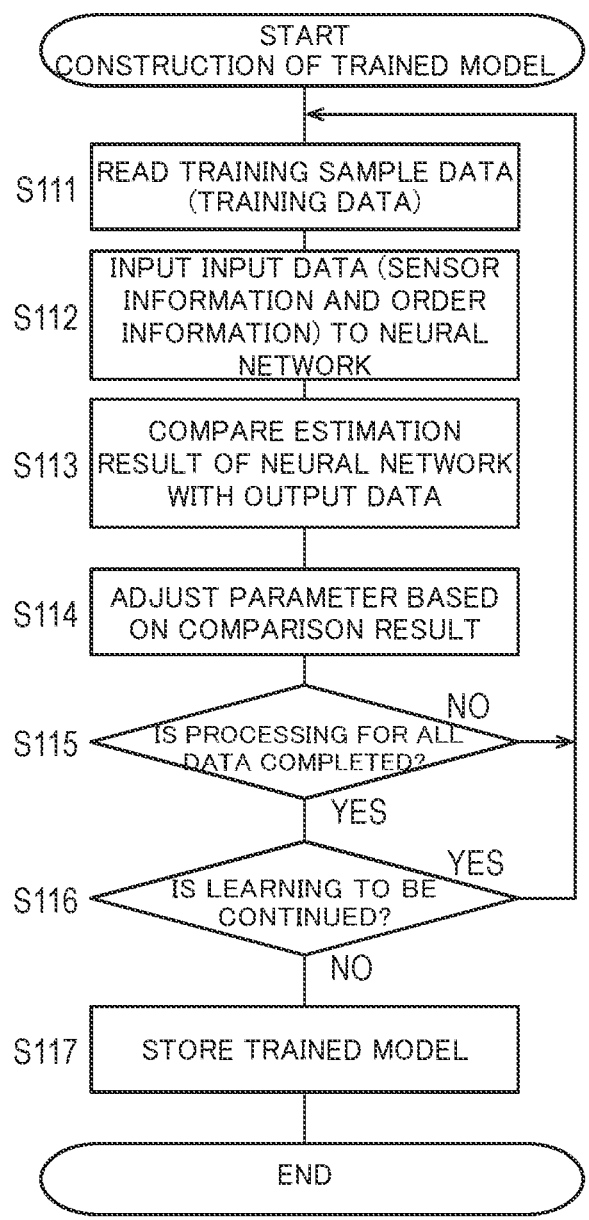
FIG. 6 is a flowchart illustrating a machine learning method for a trained model.

FIG. 6 is a flowchart illustrating the machine learning method for the trained model.

In the processing of FIG. 6, the machine learning is executed using, as training sample data, a large number of data sets (i sets (i is, for example, several thousands to several hundred thousands)) in which sensor information and order information prepared in advance are included as input and information regarding a radiographing condition is included as an output. As a learner (not illustrated) that functions as the identifier, for example, a stand-alone high-performance computer using a CPU processor and a GPU processor, or a cloud computer is used. Hereinafter, the training method using a neural network configured by combining perceptions such as deep learning for the learner will be described, but the training method is not limited to this, and various methods can be applied. For example, a random forest, a decision tree, a support vector machine (SVM), a logistic regression, a k-nearest neighbor algorithm, a topic model, or the like can be applied.
(Step S111)

The learner reads training sample data that is training data. For the first time, the first set of training sample data is read, and for the i-th time, the i-th set of training sample data is read.
(Step S112)

The learner inputs input data among the read training sample data to the neural network.
(Step S113)

The learner compares an estimation result of the neural network with correct answer data.
(Step S114)

The learner adjusts a parameter based on the comparison result. For example, the learner executes processing based on backpropagation to adjust the parameter so as to reduce a difference between the comparison results.
(Step S115)

When the processing for all the data from the first to i-th sets of data is completed (YES), the learner advances the processing to Step S116. When the processing is not completed (NO), the learner returns the processing to Step S111, reads the next training sample data, and repeats the processing of Step S111 and subsequent Steps.
(Step S116)

The learner determines whether or not to continue the learning, and in a case where the learning is to be continued (YES), the processing returns to Step S111, and in Steps S111 to S115, the processing of the first to i-th sets are executed again, and in a case where the learning is not to be continued (NO), the processing proceeds to Step S117.
(Step S117)

The learner stores the trained model constructed by the processing so far and ends the processing (End). A storage destination includes an internal memory of the console 3. In the processing of FIG. 4 described above, the radiographing condition is determined using the trained model generated in this manner.

<Effects of Console 3 and Radiographic Image Capturing System 100>

As described above, in the console 3, the sensor information and the order information are input, and the radiographing condition is determined using the trained identifier. Accordingly, it is possible to guide an appropriate radiographing condition corresponding to the radiographing order according to the state of the subject H before the radiographing. Therefore, this makes it possible to prevent the state of the subject from affecting the radiographic image. Hereinafter, this function and effect will be described in detail.

In the radiographing, a radiographer adjusts the conditions of the radiation irradiation device and the radiation detection device, and in addition to these set conditions, the state of the subject also affects the radiographic image. The state of the subject is, for example, a posture, body position, respiratory phase, and the like of the subject. For this reason, for example, there is a possibility that an appropriate radiographic image cannot be captured due to the skill, experience, and the like of the radiographer. For example, even in a case where the radiographing is performed a plurality of times with the same set conditions of the radiation irradiation device and the radiation detection device for a chest of the same subject, there is a possibility that the radiographic image varies depending on the radiographer and reproducibility cannot be secured.

On the other hand, in the radiographic image capturing system 100, the sensor information regarding the subject H immediately before the radiographing is detected using the optical camera 4, and the radiographing condition is determined based on the sensor information and the order information regarding the radiographing order. In other words, regardless of the skill, experience, and the like of the radiographer, the console 3 determines an appropriate radiographing condition in consideration of the state of the subject H, such as the body position, posture, and respiratory phase of the subject H and the radiographing order. Therefore, even in the radiographing by the radiographer having little experience, it is possible to prevent the state of the subject from affecting the radiographic image.

The sensor information includes, for example, image information. Accordingly, the console 3 can acquire various information regarding the state of the subject H.

Furthermore, the console 3 determines a radiation irradiation condition as the radiographing condition and outputs the radiation irradiation condition to the radiation irradiation device 1. By determining the irradiation condition as the radiographing condition, it is easy to capture an appropriate radiographic image.

Furthermore, the order information includes information regarding a site to be radiographed and a radiographing direction. This makes it easier for the console 3 to determine a more appropriate radiographing condition.

Note that the present invention is not limited to the above-described embodiments, and various modifications can be made within the scope of claims.

For example, each of the radiation irradiation device 1, the radiation detection device 2, the console 3, the optical camera 4, and the server 5 may include components other than the above-described components, or may not include some of the above-described components.

Furthermore, each of the radiation irradiation device 1, the radiation detection device 2, the console 3, the optical camera 4, and the server 5 may include a plurality of devices, or may include a single device.

Furthermore, the function of each configuration may be realized by another configuration. For example, the optical camera 4 and the server 5 may be integrated into the console 3, and some or all of the functions of the optical camera 4 and the server 5 may be realized by the console 3.

Furthermore, in the above-described embodiment, an example in which the radiographic image capturing system 100 includes the optical camera 4 as the sensor has been described, but the radiographic image capturing system 100 may include another sensor together with the optical camera 4 or instead of the optical camera 4. For example, the radiographic image capturing system 100 may include a distance sensor, a scale, a body fat sensor, and the like.

Furthermore, a unit of processing in the flowchart of the above-described embodiment is divided according to main processing contents in order to facilitate understanding of each processing. The present invention is not limited by the way of classifying the processing steps. Each processing can also be divided into more processing steps. Furthermore, in one processing step, much processing may be executed.

Means and the method for performing various processing in the system according to the above-described embodiment can be realized by all of a dedicated hardware circuit or a programmed computer. The program may be provided by using, for example, a computer-readable recording medium such as a flexible disk and a CD-ROM, or may be provided online via a network such as the Internet. In this case, the program stored in the computer-readable recording medium is usually transferred to and stored in a storage such as a hard disk. Furthermore, the program may be provided as independent application software, or may be incorporated into software of the device serving as one function of the system.

Although embodiments of the present invention have been described and illustrated in detail, the disclosed embodiments are made for purpose of illustration and example only and not limitation. The scope of the present invention should be interpreted by terms of the appended claims.

What is claimed is:

1. A condition determination device comprising a hardware processor that:
   acquires sensor information obtained by detecting information regarding a subject to be radiographed by using a sensor that is separate from a radiation detection device used for radiographing and order information regarding a radiographing order; and
   determines a radiographing condition by inputting said sensor information and said order information to a trained identifier.

2. The condition determination device according to claim 1, wherein said sensor information includes image information.

3. The condition determination device according to claim 2, wherein said image information includes information regarding at least one of a position of said subject, a body posture of said subject, or a site of said subject to be radiographed.

4. The condition determination device according to claim 1, wherein said sensor includes an optical camera.

5. The condition determination device according to claim 1, wherein said radiographing condition includes a radiation irradiation condition for said subject.

6. The condition determination device according to claim 5, wherein said hardware processor outputs said irradiation condition to a radiation irradiation device.

7. The condition determination device according to claim 1, wherein said order information includes information regarding at least one of a site to be radiographed or a radiographing direction.

8. A non-transitory recording medium storing a computer readable program causing a computer to perform:
   acquiring sensor information obtained by detecting information regarding a subject to be radiographed by using a sensor that is separate from a radiation detection device used for radiographing and order information regarding a radiographing order; and
   determining a radiographing condition by inputting said sensor information and said order information to a trained identifier.

9. A condition determination method comprising:
   acquiring sensor information obtained by detecting information regarding a subject to be radiographed by using a sensor that is separate from a radiation detection device used for radiographing and order information regarding a radiographing order; and
   determining a radiographing condition by inputting said sensor information and said order information to a trained identifier.

10. A condition determination device comprising a hardware processor that:
    acquires sensor information obtained by detecting information regarding a subject to be radiographed by using a sensor and order information regarding a radiographing order; and determines a radiographing condition by inputting said sensor information and said order information to a trained identifier, wherein the radiographing condition is a radiographing parameter to be used for radiographing the subject.

11. The condition determination device according to claim 10, wherein said sensor information includes image information.

12. The condition determination device according to claim 11, wherein said image information includes information regarding at least one of a position of said subject, a body posture of said subject, or a site of said subject to be radiographed.

13. The condition determination device according to claim 10, wherein said sensor includes an optical camera.

14. The condition determination device according to claim 10, wherein said radiographing condition includes a radiation irradiation condition for said subject.

15. The condition determination device according to claim 14, wherein said hardware processor outputs said irradiation condition to a radiation irradiation device.

16. The condition determination device according to claim 10, wherein said order information includes information regarding at least one of a site to be radiographed or a radiographing direction.

17. The condition determination device according to claim 10, wherein the radiographing parameter is selected from the group consisting of irradiation range, irradiation direction, irradiation dose, tube voltage value, tube current value, irradiation time, source to image receptor distance (SID), a tube current time product (mAs), and any combination thereof.

\* \* \* \* \*